United States Patent [19]
Maraskovsky et al.

[11] Patent Number: 6,017,527
[45] Date of Patent: Jan. 25, 2000

[54] ACTIVATED DENDRITIC CELLS AND METHODS FOR THEIR ACTIVATION

[75] Inventors: Eugene Maraskovsky; Hilary J. Mc Kenna, both of Seattle, Wash.

[73] Assignee: Immunex Corporation, Seattle, Wash.

[21] Appl. No.: 08/763,995

[22] Filed: Dec. 12, 1996

Related U.S. Application Data

[63] Continuation of application No. 08/677,762, Jul. 10, 1996, abandoned.

[51] Int. Cl.$^7$ .............................. A01N 63/00; C12N 5/10
[52] U.S. Cl. ........................... 424/93.71; 424/93.7; 435/2; 435/325; 435/375; 435/377; 435/455
[58] Field of Search .................... 514/2, 8, 12; 435/2, 435/325; 424/93.7

[56] References Cited

U.S. PATENT DOCUMENTS

| | | |
|---|---|---|
| 5,525,708 | 6/1996 | Nocka . |
| 5,540,926 | 7/1996 | Aruffo . |
| 5,633,234 | 5/1997 | August et al. . |

FOREIGN PATENT DOCUMENTS

| | | |
|---|---|---|
| 93/08207 | 4/1993 | WIPO . |
| 94/28113 | 12/1994 | WIPO . |

OTHER PUBLICATIONS

I. Morse et al. Cancer Research 58:2965–2968 (1998).
Grouard et al. J. Immunol. 155:3345–3352 (1995).
Calland et al. Immunol. Today 14:559–564 (1993).
Noelle et al. Immunol. Today 13:431–433 (1992).
Siena et al. Eptl. Hematol. 23:1463–1471 (1995).
Grouard et al. *J. Immunol.* 155:3345, 1995.
Van der Berg et al., *Immunol.* 88:294, 1996.
Peguet–Navarro et al., *J. Immunol* 155:4241, 1995.
Paglia et al., *J. Exp. Med.* 178:1893, 1993.
Levya–Cobian et al., *Immunology Letters* 43:29, 1994.
Girolomani et al., *Eur. J. Dermatol.* 5:12, 1995.
Jaiswal et al., *Int'l. Immunol.* 8:275, 1996.
Koch et al., *J. Exp. Med.* 184:741, 1996.
Caux et al., *J. Exp. Med.* 180:1263, 1994.
Sallusto et al., *J. Exp. Med.* 179:1109, 1994.
Ye et al., American Society of Hematology 37th Annual Meeting.
Gee et al., Keystone Mone Marrow Transplantation Symposia 1996.

*Primary Examiner*—Christina Y. Chan
*Assistant Examiner*—Phillip Gambel
*Attorney, Agent, or Firm*—Janis C. Henry

[57] ABSTRACT

Antigen-expressing, activated dendritic cells are disclosed. Such dendritic cells are used to present tumor, viral or bacterial antigens to T cells, and can be useful in vaccination protocols. Other cytokines can be used in separate, sequential or simultaneous combination with the activated, antigen-pulsed dendritic cells. Also disclosed are methods for stimulating an immune response using the antigen-expressing, activated dendritic cells.

15 Claims, 3 Drawing Sheets

FIGURE 1

TTX-specific T cell proliferation

- ●— -CD40L+TTX
- ○— +CD40L+TTX
- ▲— T cells alone

ACTIVATED DENDRITIC CELLS AND METHODS FOR THEIR ACTIVATION

This is a continuation of application Ser. No. 08/677,762, filed Jul. 10, 1996,now abandoned.

FIELD OF THE INVENTION

The present invention relates to a dendritic cell activation factor, to methods of enhancing a lymphocyte-mediated immune response in vivo, and to dendritic cell populations useful in the manipulation of cellular and humoral immune responses.

BACKGROUND OF THE INVENTION

Vaccination is an efficient means of preventing death or disability from infectious diseases. The success of this method in the field of infectious disease has also stimulated interest in utilizing vaccination in the treatment or prevention of neoplastic disease. Despite the successes achieved with the use of vaccines, however, there are still many challenges in the field of vaccine development. Parenteral routes of administration, the numbers of different vaccinations required and the need for, and frequency of, booster immunizations all impede efforts to control or eliminate disease.

One such difficulty is lack of immunogenicity in an antigen, i.e., the antigen is unable to promote an effective immune response against the pathogen. In addition, certain antigens may elicit only a certain type of immune response, for example, a cell-mediated or a humoral response. Adjuvants are substances that enhance, augment or potentiate an immune response, and can in some instances be used to promote one type of immune response over another. Although numerous vaccine adjuvants are known, alum is the only adjuvant widely used in humans.

Dendritic cells are a heterogeneous cell population with distinctive morphology and a widespread tissue distribution (Steinman, R. M., *Annu. Rev. Immunol.*, 9: 271–296, 1991). Dendritic cells are referred to as "professional" antigen presenting cells, and have a high capacity for sensitizing MHC-restricted T cells. Thus, there is growing interest in using dendritic cells ex vivo as tumor or infectious disease vaccine adjuvants (see, for example, Romani, et al., *J. Exp. Med.*, 180: 83, 1994). Therefore, an agent that enhanced the ability of dendritic cells to stimulate an immune response would be of wide importance.

SUMMARY OF THE INVENTION

The present invention pertains to a method of activating dendritic cells to enhance antigen presenting capacity. The activated, antigen-presenting dendritic cells of the invention are useful as vaccine adjuvants.

The invention also provides a method of generating large quantities of antigen-presenting dendritic cells ex vivo. Following collection of an individual's $CD34^+$ hematopoietic progenitors and stem cells, cytokines such as granulocyte-macrophage colony stimulating factor (GM-CSF) and flt-3 ligand (flt3-L) can be used to expand the cells in vitro and to drive them to differentiate into cells of the dendritic cell lineage. Cytokines can also be used to increase the numbers of $CD34^+$ cells in circulation prior to collection. The resulting dendritic cells are exposed to an antigen one wishes to elicit an immune response against, and allowed to process the antigen (this procedure is sometimes referred to in the art as "antigen-pulsing"). The antigen-pulsed (or antigen-expressing) dendritic cells are then activated with a CD40 binding protein, and subsequently administered to the individual.

An alternate method for preparing dendritic cells that present antigen is to transfect the dendritic cells with a gene encoding an antigen or a specific polypeptide derived therefrom. Once the dendritic cells express the antigen in the context of MHC, the dendritic cells are activated with a CD40 binding protein, and subsequently administered to the individual to provide a stronger and improved immune response to the antigen.

The activated antigen-presenting dendritic cells can also be used as a vaccine adjuvant and can be administered prior to, concurrently with or subsequent to antigen administration. Moreover, the dendritic cells can be administered to the individual prior to, concurrently with or subsequent to administration of cytokines that modulate an immune response, for example a CD40 binding protein (i.e., soluble CD40L), or a soluble CD83 molecule. Additional useful cytokines include, but are not limited to, Interleukins (IL) 1, 2, 4, 5, 6, 7, 10, 12 and 15, colony stimulating factors (CSF) such as GM-CSF, granulocyte colony stimulating factor (G-CSF), or GM-CSF/IL-3 fusion proteins, or other cytokines such as TNF-α or c-kit ligand. Moreover, biologically active derivatives of these cytokines; and combinations thereof will also be useful.

The invention also provides for the ex vivo preparation of antigen-specific T cells. Following the procedures described above for preparing large numbers of antigen-presenting dendritic cells ex vivo, the collected antigen-presenting dendritic cells are used to generate antigen-specific T cells from naive T cells that have been collected from the individual. After the antigen has been adequately presented to the T cells generated, the antigen-specific T cells can be administered to the individual.

DETAILED DESCRIPTION OF THE INVENTION

The invention is directed to the use of CD40L to activate antigen-pulsed dendritic cells. Activation enhances the ability of the dendritic cells to present antigen to lymphoid cells, and thus augments the immune response against the antigen. Another embodiment of the invention is the isolation and use of activated, antigen-pulsed dendritic cells as vaccine adjuvants. The activated, antigen-pulsed dendritic cells may also be used ex vivo to generate antigen-specific T cells.

Dendritic Cells

Dendritic cells comprise a heterogeneous cell population with distinctive morphology and a widespread tissue distribution. The dendritic cell system and its role in immunity is reviewed by Steinman, R. M., *Annu. Rev. Immunol.,* 9: 271–296 (1991), incorporated herein by reference. The cell surface of dendritic cells is unusual, with characteristic veil-like projections, and is characterized by having the cell surface markers $CD1a^+$, $CD4^+$, $CD86^+$, or $HLA-DR^+$. Dendritic cells have a high capacity for sensitizing MHC-restricted T cells and are very effective at presenting antigens to T cells in situ, both self-antigens during T cell development and tolerance and foreign antigens during immunity.

Because of their effectiveness at antigen presentation, there is growing interest in using dendritic cells ex vivo as tumor or infectious disease vaccine adjuvants (see, for example, Romani, et al., *J. Exp. Med.,* 180: 83 (1994). The use of dendritic cells as immunostimulatory agents has been limited due to the low frequency of dendritic cells in peripheral blood, the limited accessibility of lymphoid organs and the dendritic cells' terminal state of differentiation. Dendritic cells originate from CD34+ bone marrow or peripheral blood progenitors and peripheral blood mononuclear cells, and the proliferation and maturation of dendritic cells can be enhanced by the cytokines GM-CSF (sargramostim, Leukine®, Immunex Corporation, Seattle, Wash.), TNF-α, c-kit ligand (also known as stem cell factor (SCF), steel factor (SF), or mast cell growth factor (MGF)) and interleukin-4. Recently, flt3-L has been found to stimulate the generation of large numbers of functionally mature dendritic cells, both in vivo and in vitro (U.S. Ser. No. 08/539,142, filed Oct. 4, 1995).

Ex Vivo Culture of Dendritic Cells

A procedure for ex vivo expansion of hematopoietic stem and progenitor cells is described in U.S. Pat. No. 5,199,942, incorporated herein by reference. Other suitable methods are known in the art. Briefly, ex vivo culture and expansion comprises: (1) collecting $CD^{34}+$ hematopoietic stem and progenitor cells from a patient from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used.

Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow. Cytokines such as flt3-L may be used to increase or mobilize the numbers of dendritic cells in vivo. Increasing the quantity of an individual's dendritic cells may facilitate antigen presentation to T cells for antigen(s) that already exists within the patient, such as a tumor antigen, or a bacterial or viral antigen. Alternatively, cytokines may be administered prior to, concurrently with or subsequent to administration of an antigen to an individual for immunization purposes.

Peripheral blood cells are collected using apheresis procedures known in the art. See, for example, Bishop et al., *Blood,* vol. 83, No. 2, pp. 610–616 (1994). Briefly, peripheral blood progenitor cells (PBPC) and peripheral blood stem cells (PBSC) are collected using conventional devices, for example, a Haemonetics Model V50 apheresis device (Haemonetics, Braintree, Mass.). Four-hour collections are performed typically no more than five times weekly until approximately $6.5 \times 10^8$ mononuclear cells (MNC)/kg are collected. The cells are suspended in standard media and then centrifuged to remove red blood cells and neutrophils. Cells located at the interface between the two phases (the buffy coat) are withdrawn and resuspended in HBSS. The suspended cells are predominantly mononuclear and a substantial portion of the cell mixture are early stem cells.

A variety of cell selection techniques are known for identifying and separating $CD34^+$ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art, as are specific binding proteins therefore (see for example, U.S. Ser. No. 08/539,142, filed Oct. 4, 1995).

In one method, antibodies or binding proteins are fixed to a surface, for example, glass beads or flask, magnetic beads, or a suitable chromatography resin, and contacted with the population of cells. The stem cells are then bound to the bead matrix. Alternatively, the binding proteins can be incubated with the cell mixture and the resulting combination contacted with a surface having an affinity for the antibody-cell complex. Undesired cells and cell matter are removed providing a relatively pure population of stem cells. The specific cell binding proteins can also be labeled with a fluorescent label, e.g., chromophore or fluorophore, and the labeled cells separated by sorting. Preferably, isolation is accomplished by an immunoaffinity column.

Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. The substrate should, either by its own properties, or by the addition of a chemical moiety, display high-affinity for a moiety found on the cell-binding protein. Typical substrates include avidin and streptavidin, while other conventional substrates can be used.

In one useful method, monoclonal antibodies that recognize a cell surface antigen on the cells to be separated are typically further modified to present a biotin moiety. The affinity of biotin for avidin thereby removably secures the monoclonal antibody to the surface of a packed bed (see Berenson, et al., *J. Immunol. Meth.,* 91: 11, 1986). The packed bed is washed to remove unbound material, and target cells are released using conventional methods. Immunoaffinity columns of the type described above that utilize biotinylated anti-CD34 monoclonal antibodies secured to an avidin-coated packed bed are described for example, in WO 93/08268.

An alternative means of selecting the quiescent stem cells is to induce cell death in the dividing, more lineage-committed, cell types using an antimetabolite such as 5-fluorouracil (5-FU) or an alkylating agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., *Science,* 267: 104 (1995), which is incorporated herein by reference.

Isolated stem cells can be frozen in a controlled rate freezer (e.g., Cryo-Med, Mt. Clemens, Mich.), then stored in the vapor phase of liquid nitrogen using dimethylsulfoxide as a cryoprotectant. A variety of growth and culture media can be used for the growth and culture of dendritic cells (fresh or frozen), including serum-depleted or serum-based media. Useful growth media include RPMI, TC 199, Iscoves modified Dulbecco's medium (Iscove, et al., *F.J. Exp. Med.,* 147: 923 (1978)), DMEM, Fischer's, alpha medium, NCTC, F-10, Leibovitz's L-15, MEM and McCoy's.

Particular nutrients present in the media include serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, or Tris, that acts to stabilize the pH of the media, and various inorganic salts. A variety of serum-free cellular growth media is described in WO 95/00632, which is incorporated herein by reference.

The collected $CD34^+$ cells are cultured with suitable cytokines, for example, as described herein, and in U.S. Ser. No. 08/539,142. $CD34^+$ cells then are allowed to differentiate and commit to cells of the dendritic lineage. These cells are then further purified by flow cytometry or similar means, using markers characteristic of dendritic cells, such as CD1a, HLA DR, CD80 and/or CD86. The cultured dendritic cells are exposed to an antigen, for example, a tumor antigen or an antigen derived from a pathogenic or opportunistic organism, allowed to process the antigen, and then cultured with an amount of a CD40 binding protein to activate the dendritic cell. Alternatively, the dendritic cells are transfected with a gene encoding an antigen, and then cultured with an amount of a CD40 binding protein to activate the antigen-presenting dendritic cells.

The activated, antigen-carrying dendritic cells are them administered to an individual in order to stimulate an antigen-specific immune response. The dendritic cells can be administered prior to, concurrently with, or subsequent to, antigen administration. Alternatively, T cells may be collected from the individual and exposed to the activated, antigen-carrying dendritic cells in vitro to stimulate antigen-specific T cells, which are administered to the individual.

Useful Cytokines

Various cytokines will be useful in the ex vivo culture of dendritic cells. Flt3-L refers to a genus of polypeptides that are described in EP 0627487 A2 and in WO 94/28391, both incorporated herein by reference. A human flt3-L cDNA was deposited with the American Type Culture Collection, Rockville, Md., USA (ATCC) on Aug. 6, 1993 and assigned accession number ATCC 69382. IL-3 refers to a genus of interleukin-3 polypeptides as described in U.S. Pat. No. 5,108,910, incorporated herein by reference. A DNA sequence encoding human IL-3 protein suitable for use in the invention is publicly available from the American Type Culture Collection (ATCC) under accession number ATCC 67747. c-kit ligand is also referred to as Mast Cell Growth Factor (MGF), Steel Factor or Stem Cell Factor (SCF), and is described in EP 423,980, which is incorporated herein by reference.

Other useful cytokines include Interleukin-4 (IL-4; Mosley et al., *Cell* 59: 335 (1989), Idzerda et al., *J. Exp. Med.* 171: 861 (1990) and Galizzi et al., *Intl. Immunol.* 2: 669 (1990), each of which is incorporated herein by reference) and granulocyte-macrophage colony stimulating factor (GM-CSF; described in U.S. Pat. Nos. 5,108,910, and 5,229, 496 each of which is incorporated herein by reference). Commercially available GM-CSF (sargramostim, Leukine®) is obtainable from Immunex Corp., Seattle, Wash.). Moreover, GM-CSF/IL-3 fusion proteins (i.e., a C-terminal to N-terminal fusion of GM-CSF and IL-3) will also be useful in ex vivo culture of dendritic cells. Such fusion proteins are known and are described in U.S. Pat. Nos. 5,199,942, 5,108,910 and 5,073,627, each of which is incorporated herein by reference. A preferred fusion protein is PIXY321 as described in U.S. Pat. No. 5,199,942.

In addition to their use in ex vivo culture of dendritic cells, cytokines will also be useful in the present invention by separate, sequential or simultaneous administration of a cytokine or cytokines with activated, antigen-pulsed dendritic cells. Preferred cytokines are those that modulate an immune response, particularly cytokines selected from the group consisting of Interleukins 1, 2, 3, 4, 5, 6, 7, 10, 12 and 15; granulocyte-macrophage colony stimulating factor, granulocyte colony stimulating factor; a fusion protein comprising Interleukin-3 and granulocyte-macrophage colony stimulating factor; Interferon-γ; TNF; TGF-β; flt-3 ligand; soluble CD40 ligand; biologically active derivatives of these cytokines; and combinations thereof. Soluble CD83, described in U.S. Ser. No. 08/601,954, filed Feb. 15, 1996), and soluble CD40L (described in U.S. Ser. No. 08/477,733 and U.S. Ser. No. 08/484,624, both filed Jun. 7, 1995) are particularly preferred cytokines.

Useful cytokines act by binding a receptor present on the surface of a dendritic cell and transducing a signal. Moreover, additional binding proteins can be prepared as described herein for CD40 binding proteins, that bind appropriate cytokine receptors and transduce a signal to a dendritic cell. For example, WO 95/27062 describes agonistic antibodies to Flt-3, the receptor for Flt-3L, from which various Flt-3 binding proteins can be prepared. Additional useful cytokines include biologically active analogs of cytokines that are useful for culturing dendritic cells. Useful cytokine analogs have an amino acid sequence that is substantially similar to the native cytokine, and are biologically active capable of binding to their specific receptor and transducing a biological signal. Such analogs can be prepared and tested by methods that are known in the art and as described herein.

CD40/CD40L

CD40 is a member of the tumor necrosis factor (TNF)/ nerve growth factor (NGF) receptor family, which is defined by the presence of cysteine-rich motifs in the extracellular region (Smith et al., *Science* 248: 1019, 1990; Mallett and Barclay, *Immunology Today* 12: 220; 1991). This family includes the lymphocyte antigen CD27, CD30 (an antigen found on Hodgkin's lymphoma and Reed-Sternberg cells), two receptors for TNF, a murine protein referred to as 4-1BB, rat OX40 antigen, NGF receptor, and Fas antigen. Human CD40 antigen (CD40) is a peptide of 277 amino acids having a molecular weight of 30,600 (Stamenkovic et al., *EMBO J.* 8: 1403, 1989).

Activated CD4+ T cells express high levels of a ligand for CD40 (CD40L). Human CD40L was cloned from peripheral blood T-cells as described in Spriggs et al., *J. Exp. Med.* 176: 1543 (1992). The cloning of murine CD40L is described in Armitage et al., *Nature* 357: 80 (1992). CD40L is a type II membrane polypeptide having an extracellular region at its C-terminus, a transmembrane region and an intracellular region at its N-terminus. CD40L biological activity is mediated by binding of the extracellular region of CD40L with CD40, and includes B cell proliferation and induction of antibody secretion (including IgE secretion).

CD40L is believed to be important in feedback regulation of an immune response. For example, a CD40+ antigen presenting cell will present antigen to a T cell, which will then become activated and express CD40L. The CD40L will, in turn, further activate the antigen presenting cell, increasing its efficiency at antigen presentation, and upregulating expression of Class I and Class II MHC, CD80 and CD86 costimulatory molecules, as well as various cytokines (Caux et al., *J. Exp. Med.* 180: 1263, 1994).

Useful forms of CD40L for the inventive methods as disclosed in U.S. Ser. No. 08/477,733 and U.S. Ser. No. 08/484,624, both filed Jun. 7, 1995, and both of which are incorporated by reference herein. Such useful forms include soluble, oligomeric CL40 ligand comprising a CD40-binding peptide and an oligomer-forming peptide. The CD40-binding peptide is selected from the group consisting of:

(a) a peptide comprising amino acids 1 through 261, 35 through 261, 34 through 225, 113 through 261, 113 through 225, 120 through 261, or 120 through 225 of SEQ ID NO:2;

(b) fragments of a peptide according to (a) that bind CD40; and (c) peptides encoded by DNA which hybridizes to a DNA that encodes a peptide of (a) or (b), under stringent conditions (hybridization in 6× SSC at 63° C. overnight; washing in 3× SSC at 55° C.), and which bind to CD40, Useful oligomer-forming peptides are also disclosed in U.S. Ser. No. 08/477,733 and U.S. Ser. No. 08/484,624, and exemplified in SEQ ID NOs: 3 and 4 herein CD40 polypeptides may exist as oligomers, such as dimers or trimers. Oligomers are linked by disulfide bonds formed between cysteine residues on different CD40L polypeptides. Alternatively, one can link two soluble CD40L domains with a $GlY_4SerGly_5Ser$ linker sequence, or other linker sequence described in U.S. Pat. No. 5,073,627, which is incorporated by reference herein. CD40L polypeptides may also be created by fusion of the C terminal of soluble CD40L to the Fc region of IgG1. CD40L/Fc fusion proteins are allowed to assemble much like heavy chains of an antibody molecule to form divalent CD40L. If fusion proteins are made with both heavy and light chains of an antibody, it is possible to form a CD40L oligomer with as many as four CD40L extracellular regions.

A corresponding family of ligands exists for molecules in the TNFR family, and several of these are also expressed on activated T cells or other cells of the immune system. This family includes tumor necrosis factor and lymphotoxin (TNF and LT, respectively; reviewed in Ware et al., *Curr. Top. Microbiol. Immunol.* 198: 175, 1995), as well as CD27L (U.S. Ser. No. 08/106,507, filed Aug. 13, 1993), CD30L (U.S. Pat. No. 5,480,981, issued Jan. 2, 1996), 4-1BBL (U.S. Ser. No. 08/236,918, filed May 6, 1994), OX40L (U.S. Pat. No. 5,457,035, issued Oct. 10, 1995) and Fas L (U.S. Ser. No. 08/571,579, filed Dec. 13, 1995). These ligands are also known to be involved in modulation of an immune response, and are likely to be useful to activate antigen-pulsed dendritic cells or other antigen presenting cells that bear the corresponding receptor.

CD40 Monoclonal Antibodies and Additional CD40 Binding Proteins

Useful CD40 binding proteins are those that are capable of binding CD40 and inhibiting binding of CD40 to CD40L, as determined by observing at least about 90% inhibition of the binding of soluble CD40 to CD40L, and include monoclonal antibodies, CD40 ligand, and molecules derived therefrom. Monoclonal antibodies directed against the CD40 surface antigen (CD40 mAb) have been shown to mediate various biological activities on human B cells (see for example, LEUKOCYTE TYPING IV; A. J. McMichael ed. Oxford University Press. Oxford, p. 426). U.S. Ser. No. 08/130, 541, filed Oct. 1, 1993, the relevant disclosure of which is incorporated by reference, discloses two monoclonal antibodies that specifically bind CD40, referred to as hCD40m2 and hCD40m3. Unlike other CD40 mAb, hCD40m2 (ATCC HB 11459; deposited under terms of the Budapest Treaty with the American Type Culture Collection in Rockville, Md., USA, on Oct. 6, 1993) and hCD40m3 bind CD40 and inhibit binding of CD40 to cells that constitutively express CD40L, indicating that hCD40m2 and hCD40m3 bind CD40 in or near the ligand binding domain.

Additional CD40 monoclonal antibodies may be generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Monoclonal antibodies that bind CD40 in or near the ligand binding domain will also be useful in the present invention.

Additional CD40 binding proteins may also be constructed utilizing recombinant DNA techniques. For example, the variable regions of a gene which encodes an antibody to CD40 that binds in or near the ligand binding domain can be incorporated into a useful CD40 binding protein (see Larrick et al., *Biotechnology* 7: 934, 1989; Reichmann et al., *Nature* 332: 323, 1988; Roberts et al., *Nature* 328: 731, 1987; Verhoeyen et al., *Science* 239: 1534, 1988; Chaudhary et al., *Nature* 339: 394, 1989).

Briefly, DNA encoding the antigen-binding site (or CD40 binding domain; variable region) of a CD40 mAb is isolated, amplified, and linked to DNA encoding another protein, for example a human IgG (see Verhoeyen et al., supra; see also Reichmann et al., supra). Alternatively, the antigen-binding site (variable region) may be either linked to, or inserted into, another completely different protein (see Chaudhary et al., supra), resulting in a new protein with antigen-binding sites of the antibody as well as the functional activity of the completely different protein.

Similarly, the CD40 binding region (extracellular domain) of a CD40 ligand may be used to prepare other CD40 binding proteins. Useful forms of CD40 ligand are disclosed in U.S. Ser. No. 08/477,733 and U.S. Ser. No. 08/484,624, both of which were filed on Jun. 7, 1995. Additional forms of CD40 ligand can be prepared by methods known in the art. As for other useful CD40 binding proteins, CD40 ligand will bind CD40 in or near the ligand binding domain, and will be capable of transducing a signal to a cell expressing CD40 (i.e., biologically active).

DNA sequences that encode proteins or peptides that form oligomers will be particularly useful in preparation of CD40 binding proteins comprising an antigen binding domain of CD40 antibody, or an extracellular domain of a CD40 ligand. Certain of such oligomer-forming proteins are disclosed in U.S. Ser. No. 08/477,733 and U.S. Ser. No. 08/484,624, both of which were filed on Jun. 7, 1995; additional, useful oligomer-forming proteins are also disclosed in U.S. Ser. No. 08/446,922, filed May 18, 1995. Fc fusion proteins (including those that are formed with Fc muteins have decreased affinity for Fc receptors) can also be prepared.

Mutant forms of CD40 binding proteins that are substantially similar (i.e., those having an amino acid sequence at least 80% identical to a native amino acid sequence, most preferably at least 90% identical) to the previously described CD40 binding proteins will also be useful in the present invention. The percent identity may be determined, for example, by comparing sequence information using the GAP computer program, version 6.0 described by Devereux et al. (*Nucl. Acids Res.* 12: 387, 1984) and available from the University of Wisconsin Genetics Computer Group (UWGCG). The GAP program utilizes the alignment method of Needleman and Wunsch (*J. Mol. Biol.* 48: 443, 1970), as revised by Smith and Waterman (*Adv. Appl. Math* 2: 482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids* Res. 14: 6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Generally, substitutions of different amino acids from those in the native form of a useful CD40 binding protein should be made conservatively; i.e., the most preferred substitute amino acids are those which do not affect the ability of the inventive proteins to bind CD40 in a manner substantially equivalent to that of native CD40 ligand. Examples of conservative substitutions include substitution of amino acids outside of the binding domain(s), and substitution of amino acids that do not alter the secondary and/or tertiary structure of CD40 binding proteins. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Similarly, when a deletion or insertion strategy is adopted, the potential effect of the deletion or insertion on biological activity should be considered. Subunits of CD40 binding proteins may be constructed by deleting terminal or internal residues or sequences. Additional guidance as to the types of mutations that can be made is provided by a comparison of the sequence of CD40 binding proteins to proteins that have similar structures Mutations must, of course, preserve the reading frame phase of the coding sequences and preferably will not create complementary regions that could hybridize to produce secondary mRNA structures such as loops or hairpins which would adversely affect translation of the CD40 binding protein mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated proteins screened for the desired activity.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42: 133, 1986); Bauer et al. (*Gene* 37: 73, 1985); Craik (*BioTechniques*, Jan. 12–19 1985,); Smith et al. (*Genetic Engineering: Principles and Methods,* Plenum Press, 1981); and U.S. Pat. Nos. 4,518,584 and 4,737,462 disclose suitable techniques, and are incorporated by reference herein.

As is well-known in the art, not all mutations will cause a change in amino acid sequence. Mutations that confer advantageous properties in the production of recombinant proteins will also be useful for preparing useful CD40 binding proteins. Naturally occurring variants are also encompassed by the invention. Examples of such variants are proteins that result from alternate MRNA splicing events or from proteolytic cleavage of the protein, wherein the native biological property is retained.

Once suitable antibodies or binding proteins have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques. Recombinant CD40 binding proteins can be prepared according to standard methods, and tested for binding specificity to CD40 utilizing assays known in the art, including for example ELISA, ABC, or dot blot assays, as well by bioactivity assays. The latter will also be useful in evaluating the biological activity of CD40 binding proteins.

Preparation of Antigens

Immunization is a centuries old, and highly effective, means of inducing a protective immune response against pathogens in order to prevent or ameliorate disease. The vaccines that have been used for such induction are generally live, attenuated microorganisms, or preparations of killed organisms or fractions thereof. Live, attenuated vaccines are generally thought to more closely mimic the immune response that occurs with a natural infection than do those prepared from killed microbes or non-infective preparations derived from pathogens (i.e., toxoids, recombinant protein vaccines). However, attenuated vaccines also present a risk of reversion to pathogenicity, and can cause illness, especially in immunocompromised individuals.

Along with improved sanitation, immunization has been the most efficient means of preventing death or disability from numerous infectious diseases in humans and in other animals. Vaccination of susceptible populations has been responsible for eliminating small pox world wide, and for drastic decreases in the occurrence of such diseases as diphtheria, pertussis, and paralytic polio in the developed nations. Numerous vaccines are licensed for administration to humans, including live virus vaccines for certain adenoviruses, measles, mumps and rubella viruses, and poliovirus, diphtheria and tetanus toxoid vaccines, and Haemophilus b and meningococcal polysaccharide vaccines (Hinman et al., in *Principles and Practice of Infectious Diseases,* 3rd edition; G. L. Mandell, R. G. Douglas and J. E. Bennett, eds., Churchill Livingstone Inc., NY, N.Y.; 2320–2333; Table 2).

In addition to use in the area of infectious disease, vaccination is also considered a promising therapy for cancer. For such uses, tumor-associated antigens can be prepared from tumor cells, either by preparing crude lysates of tumor cells, for example as described in Cohen et al., *Cancer Res.* 54: 1055 (1994) and Cohen et al., *Eur. J. Immunol.* 24: 315 (1994), or by partially purifying the antigens (for example, as described by Itoh et al., *J. Immunol.* 153: 1202; 1994). Moreover, useful tumor antigens may be purified further, or even expressed recombinantly, to provide suitable antigen preparations. Any other methods of identifying and isolating antigens against which an immune response would be beneficial in cancer will also find utility in the inventive methods.

Purified dendritic cells are then pulsed with (exposed to) antigen, to allow them to take up the antigen in a manner suitable for presentation to other cells of the immune systems. Antigens are classically processed and presented through two pathways. Peptides derived from proteins in the cytosolic compartment are presented in the context of Class I MHC molecules, whereas peptides derived from proteins that are found in the endocytic pathway are presented in the context of Class II MHC. However, those of skill in the art recognize that there are exceptions; for example, the response of $CD8^+$ tumor specific T cells, which recognize exogenous tumor antigens expressed on MHC Class I. A review of MHC-dependent antigen processing and peptide presentation is found in Germain, R. N., *Cell* 76: 287 (1994).

Numerous methods of pulsing dendritic cells with antigen are known; those of skill in the art regard development of suitable methods for a selected antigen as routine experimentation. In general, the antigen is added to cultured dendritic cells under conditions promoting viability of the cells, and the cells are then allowed sufficient time to take up and process the antigen, and express antigen peptides on the cell surface in association with either Class I or Class II MHC, a period of about 24 hours (from about 18 to about 30 hours, preferably 24 hours). Dendritic cells may also be exposed to antigen by transfecting them with DNA encoding the antigen. The DNA is expressed, and the antigen is presumably processed via the cytosolic/Class I pathway.

Administration of Activated, Antigen-Pulsed Dendritic Cells

The present invention provides methods of using therapeutic compositions comprising activated, antigen-pulsed dendritic cells. The use of such cells in conjunction with soluble cytokine receptors or cytokines, or other immunoregulatory molecules is also contemplated. The inventive compositions are administered to stimulate an immune response, and can be given by bolus injection, continuous infusion, sustained release from implants, or other suitable technique. Typically, the cells on the inventive methods will be administered in the form of a composition comprising the antigen-pulsed, activated dendritic cells in conjunction with physiologically acceptable carriers, excipients or diluents. Such carriers will be nontoxic to recipients at the dosages and concentrations employed. Neutral buffered saline or saline mixed with conspecific serum albumin are exemplary appropriate diluents.

For use in stimulating a certain type of immune response, administration of other cytokines along with activated, antigen-pulsed dendritic cells is also contemplated. Several useful cytokines (or peptide regulatory factors) are discussed in Schrader, J. W. (*Mol Immunol* 28: 295; 1991). Such factors include (alone or in combination) Interleukins 1, 2, 4, 5, 6, 7, 10, 12 and 15; granulocyte-macrophage colony stimulating factor, granulocyte colony stimulating factor; a fusion protein comprising Interleukin-3 and granulocyte-macrophage colony stimulating factor; Interferon-γ, TNF, TGF-β, flt-3 ligand and biologically active derivatives thereof. A particularly preferred cytokine is CD40 ligand (CD40L). A soluble form of CD40L is described in U.S. Ser. No. 08/484,624, filed Jun. 7, 1995. Other cytokines will also be useful, as described herein. DNA encoding such cytokines will also be useful in the inventive methods, for example, by transfecting the dendritic cells to express the cytokines. Administration of these immunomodulatory molecules includes simultaneous, separate or sequential administration with the cells of the present invention.

The relevant disclosures of all publications cited herein are specifically incorporated by reference. The following examples are provided to illustrate particular embodiments and not to limit the scope of the invention.

EXAMPLE 1

This Example describes a method for generating purified dendritic cells ex vivo. Human bone marrow is obtained, and cells having a $CD34^+$ phenotype are isolated using a CD34 antibody column (CellPro, Bothell, Wash.). The $CD34^+$ cells are cultured in a suitable medium, for example, McCoy's enhanced media, that contains cytokines that promote the growth of dendritic cells (i.e., 20 ng/ml each of GM-CSF, IL-4, TNF-α, or 100 ng/ml flt3-L or c-kit ligand, or combinations thereof). The culture is continued for approximately two weeks at 37° C. in 10% $CO_2$ in humid air. Cells then are sorted by flow cytometry using antibodies for $CD1a^+$, $HLA-DR^+$ and $CD86^+$. A combination of GM-CSF, IL-4 and TNF-α can yield a six to seven-fold increase in the number of cells obtained after two weeks of culture, of which 50–80% of cells are $CD1a^+HLA-DR^+CD86^+$. The addition of flt3-L and/or c-kit ligand further enhances the expansion of total cells, and therefore of the dendritic cells. Phenotypic analysis of cells isolated and cultured under these conditions indicates that between 60–70% of the cells are $HLA-DR^+$, $CD86^+$, with 40–50% of the cells expressing CD1a in all factor combinations examined.

EXAMPLE 2

This Example describes a method for collecting and expanding dendritic cells. Prior to cell collection, flt3-L or sargramostim (Leukine®, Immunex Corporation, Seattle, Wash.) may be administered to an individual to mobilize or increase the numbers of circulating PBPC and PBSC. Other growth factors such as CSF-1, GM-CSF, c-kit ligand, G-CSF, EPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF and combinations thereof, can be likewise administered in sequence, or in concurrent combination with flt3-L.

Mobilized or non-mobilized PBPC and PBSC are collected using apheresis procedures known in the art. See, for example, Bishop et al., *Blood*, vol. 83, No. 2, pp. 610–616 (1994). Briefly, PBPC and PBSC are collected using conventional devices, for example, a Haemonetics Model V50 apheresis device (Haemonetics, Braintree, Mass.). Four-hour collections are performed typically no more than five times weekly until approximately $6.5 \times 10^8$ mononuclear cells (MNC)/kg individual are collected.

Aliquots of collected PBPC and PBSC are assayed for granulocyte-macrophage colony-forming unit (CFU-GM) content. Briefly, MNC (approximately 300,000) are isolated, cultured at 37° C. in 5% $CO_2$ in fully humidified air for about two weeks in modified McCoy's 5A medium, 0.3% agar, 200 U/ml recombinant human GM-CSF, 200 u/ml recombinant human IL-3, and 200 u/ml recombinant human G-CSF. Other cytokines, including flt3-L or GM-CSF/IL-3 fusion molecules (PIXY 321), may be added to the cultures. These cultures are stained with Wright's stain, and CFU-GM colonies are scored using a dissecting microscope (Ward et al., *Exp. Hematol.*, 16: 358 (1988). Alternatively, CFU-GM colonies can be assayed using the CD34/CD33 flow cytometry method of Siena et al., Blood, Vol. 77, No. 2, pp 400–409 (1991), or any other method known in the art.

CFU-GM containing cultures are frozen in a controlled rate freezer (e.g., Cryo-Med, Mt. Clemens, Mich.), then stored in the vapor phase of liquid nitrogen. Ten percent dimethylsulfoxide can be used as a cryoprotectant. After all collections from the individual have been made, CFU-GM containing cultures are thawed and pooled, then contacted with flt3-L either alone, sequentially or in concurrent combination with other cytokines listed above to drive the CFU-GM to dendritic cell lineage. The dendritic cells are cultured and analyzed for percentage of cells displaying selected markers as described above.

EXAMPLE 3

This example illustrates the ability of CD40L-stimulated dendritic cells to present allo-antigen and therefore cause proliferation of T cells. CD34+ cells were obtained from the bone marrow of a human donor, cultured for two weeks in the presence of selected cytokines, and isolated by flow cytometry substantially as described in Example 1. Prior to their use in a mixed lymphocyte reaction (MLR), the dendritic cells were cultured for an additional 24 hours in the presence or absence of a soluble trimeric form of CD40L (1 μg/ml) in McCoy's enhanced media containing cytokines that support the growth of dendritic cells.

T cells were purified from the blood of a non-HLA matched donor by rosetting with 2-aminoethylisothiouronium bromide hydrobromide-treated sheep red blood cells. CD4+ and CD8+ populations were further purified using immunomagnetic selection using a MACS (Milenyi Biotec, Sunnyvale, Calif.) according to the manufacturer's protocol. Cell proliferation assays were conducted with the purified T cells in RPMI (10% heat-inactivated fetal bovine serum (FBS)), in the presence of titrated numbers of the dendritic cells, at 37° C. in a 10% $CO_2$ atmosphere. Approximately $1 \times 10^5$ T cells per well were cultured in triplicate in round-bottomed 96-well microtiter plates (Corning) for seven days, in the presence of varying numbers of the unmatched dendritic cells. The cells were pulsed with 1 μCi/well of tritiated thymidine (25 Ci/nmole, Amersham, Arlington Heights, Ill.) for the final eight hours of culture.

Figure 1:
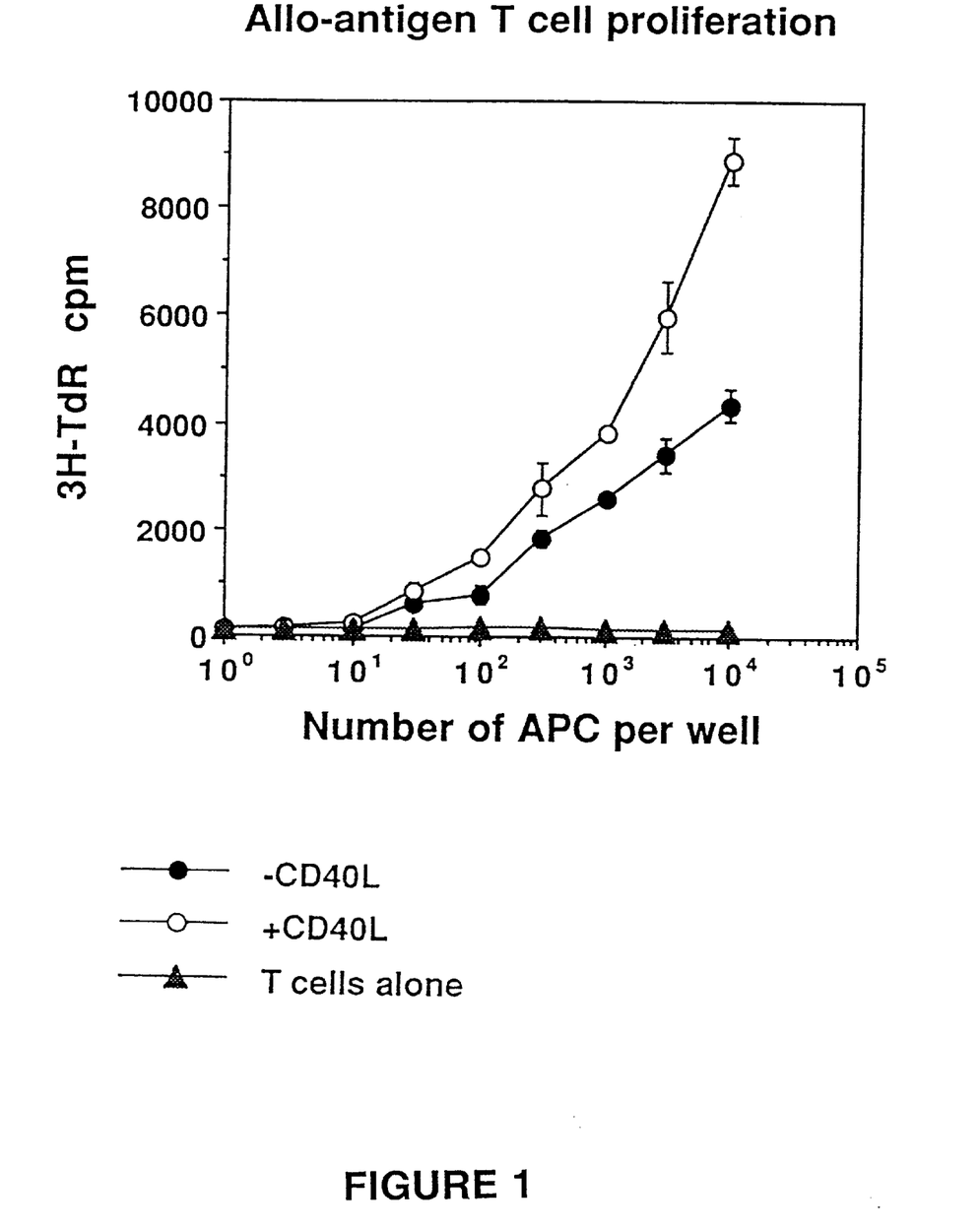
FIG. 1 presents the results of an allo-antigen T cell proliferation assay, demonstrating that incubation of dendritic cells with CD40L prior to their use in an MLR (mixed lymphocyte reaction) increases the ability of the dendritic cells to stimulate the proliferation of T cells by about threefold, as described in Example 3.

Cells were harvested onto glass fiber discs with an automated cell harvester and incorporated cpm were measured by liquid scintillation spectrometry. The results, which are shown in FIG. 1, demonstrated that three-fold fewer CD40L-activated dendritic cells were required to stimulate the equivalent proliferation of T cells compared to dendritic cells that had not been exposed to CD40L prior to their use in an MLR. This increase was most likely due to increased expression of cell surface molecules that stimulate alloreactive T cells.

EXAMPLE 4

This example illustrates the ability of dendritic cells to stimulate antigen-specific proliferation of T cells. CD34+ cells were obtained from the bone marrow of a human donor believed to be reactive against tetanus toxoid, cultured for two weeks in the presence of selected cytokines, and isolated by flow cytometry substantially as described in Example 1. Prior to their use in a tetanus toxid (TTX) antigen presentation assay, the dendritic cells were cultured for an additional 24 hours in the presence or absence of a soluble trimeric form of CD40L (1 μg/ml) in McCoy's enhanced media containing cytokines that support the growth of dendritic cells, then pulsed with purified TTX (Connaught Laboratory Inc., Swiftwater, Pa.), at 37° C. in a 10% $CO_2$ atmosphere for 24 hrs.

Autologous tetanus toxoid-reactive T cells were derived by culturing the CD34⁻ cells that were eluted from the CD34 antibody column in the presence of purified TTX and low concentrations of IL-2 and IL-7 (2 ng/ml and 5 ng/ml, respectively) for two weeks. The CD34⁻ population contains a percentage of T cells (about 5%), a proportion of which are reactive against tetanus toxoid, as well as other cell types that act as antigen presenting cells. By week 2, analysis of these cells indicated that they were about 90% T cells, the majority of which were tetanus toxoid-specific, with low levels of the T cell activation markers.

Figure 2:
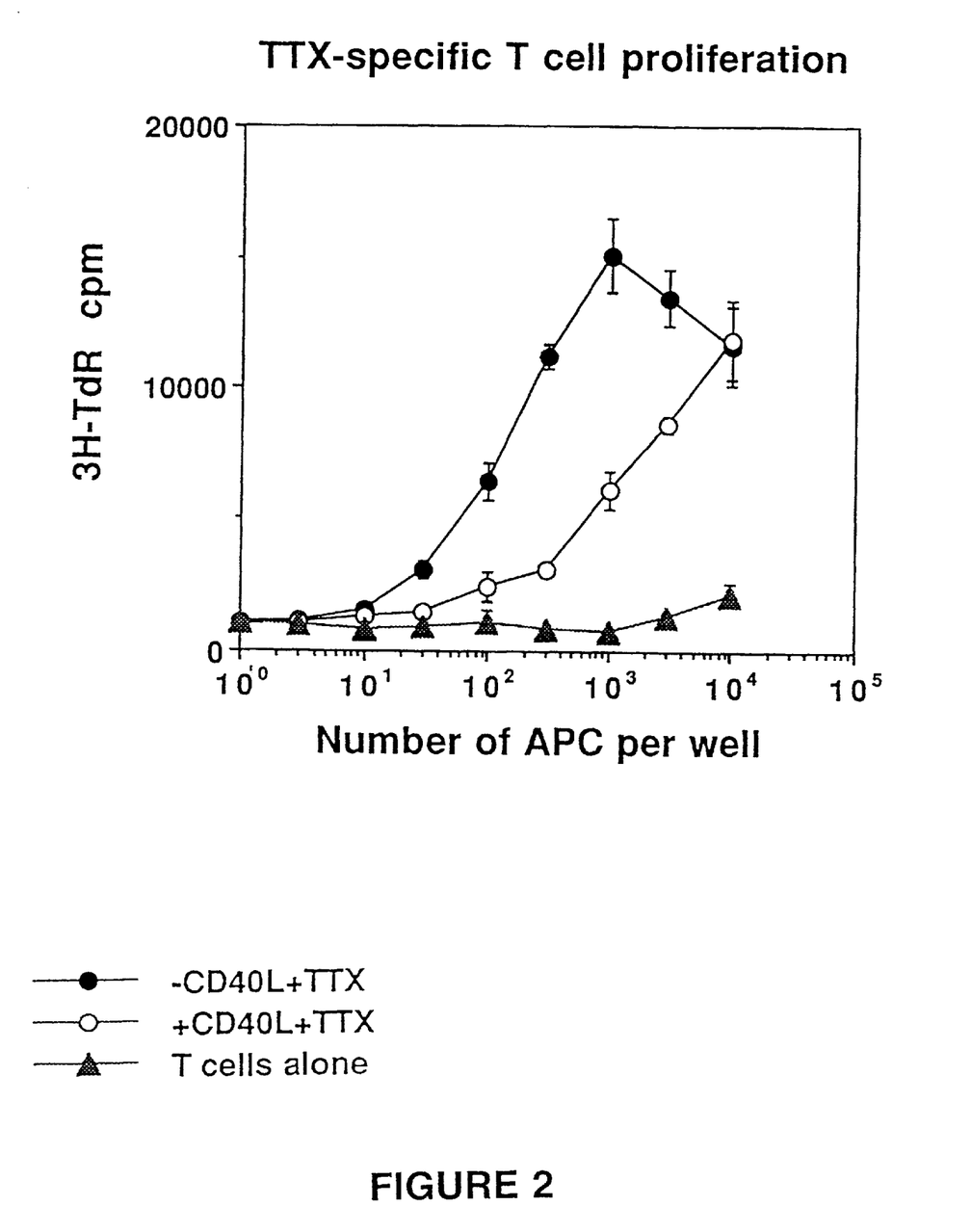
FIG. 2 illustrates that dendritic cells that are cultured with CD40L are less effective at presenting antigen to antigen-specific T cells than dendritic cells that were not exposed to CD40L, as described in Example 4.

Antigen specific T cell proliferation assays were conducted with TTX-specific T cells from CD34⁻ bone marrow cells as above, in RPMI with added 10% heat-inactivated fetal bovine serum (FBS), in the presence of the tetanus toxoid-pulsed dendritic cells, at 37° C. in a 10% $CO_2$ atmosphere. Approximately $1 \times 10^5$ T cells per well were cultured in triplicate in round-bottomed 96-well microtiter plates (Corning) for five days, in the presence of a titrated number of dendritic cells. The cells were pulsed with 1 μCi/well of tritiated thymidine (25 Ci/nmole, Amersham, Arlington Heights, Ill.) for the final four to eight hours of culture. Cells were harvested onto glass fiber discs with an automated cell harvester and incorporated cpm were measured by liquid scintillation spectrometry. The results, which are shown in FIG. 2, indicated that dendritic cells that are cultured with CD40L are about ten-fold less efficient at presenting antigen to TTX-specific T cells than dendritic cells that were not exposed to CD40L.

EXAMPLE 5

Figure 3:
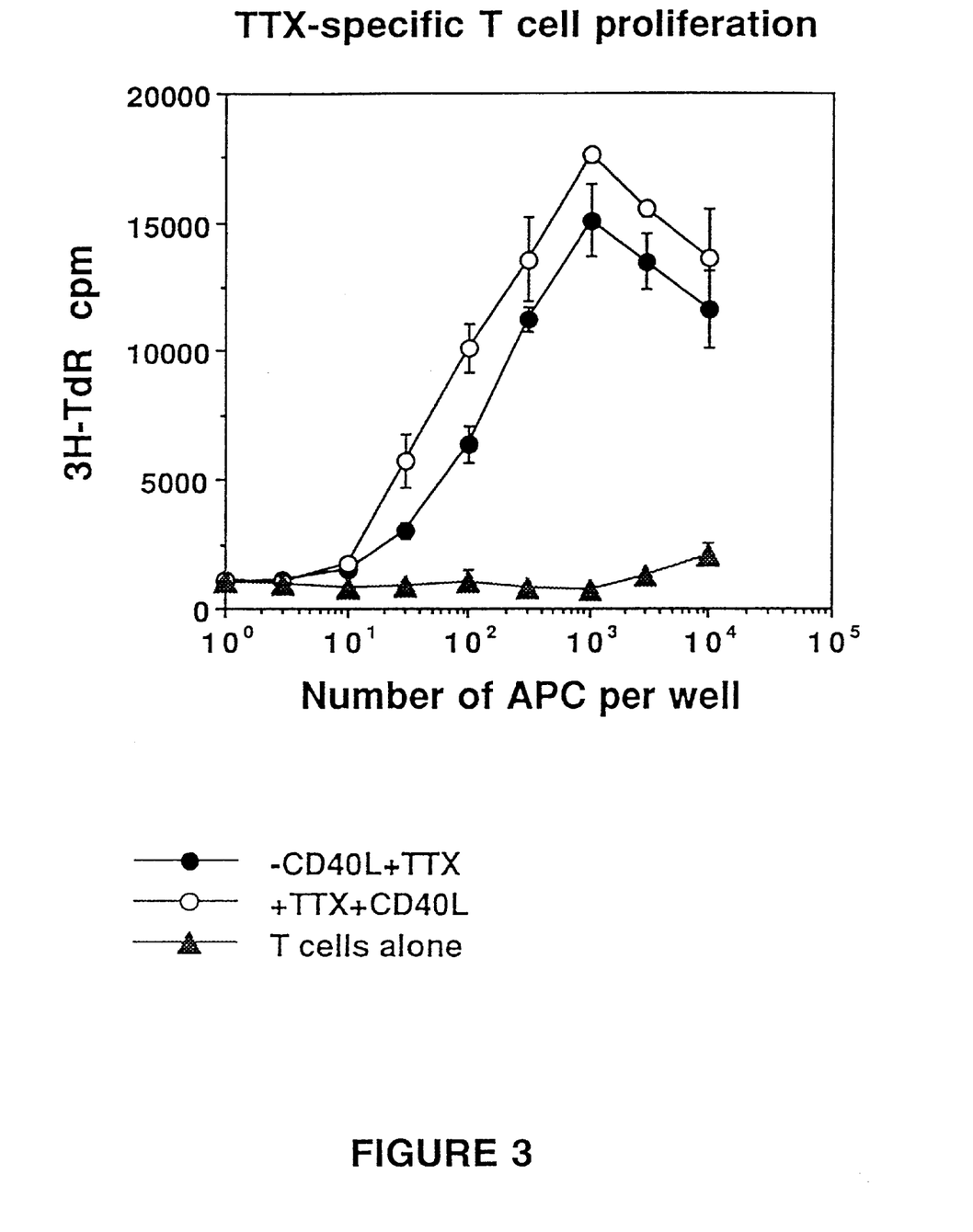
FIG. 3 demonstrates that that dendritic cells that are first pulsed with antigen, then cultured with CD40L are more effective at presenting antigen to antigen-specific T cells than dendritic cells that were pulsed with antigen but not exposed to CD40L, as described in Example 5.

This example illustrates the ability of CD40L to activate antigen-pulsed dendritic cells for stimulation of antigen-specific T cells. CD34+ cells were obtained and treated as described in Example 4, except that the cells were pulsed with tetanus toxoid for 24 hours prior to culture with CD40L. Autologous tetanus toxoid-reactive T cells were derived, and antigen specific T cell proliferation assays conducted, as described in Example 4. The results, which are shown in FIG. 3, indicated that three-fold fewer dendritic cells that are first pulsed with antigen, then cultured with CD40L, were required to stimulate the equivalent level of proliferation when presenting TTX to TTX-specific T cells than dendritic cells that were pulsed with antigen but not exposed to CD40L.

What is claimed is:

1. A method of stimulating an immune response specific for an antigen in an individual, comprising the steps of:

(a) obtaining dendritic cells from the individual;

(b) transfecting the dendritic cells with a gene encoding the antigen;

(c) activating the transfected dendritic cells by exposing them to a CD40 binding protein capable of binding CD40 and inhibiting binding of CD40 to CD40L, as determined by observing at least about 90% inhibition of the binding of soluble CD40 to CD40L; and, (d) administering the activated, antigen-expressing dendritic cells to the individual.

2. The method according to claim 1, wherein the dendritic cells are obtained by obtaining hematopoietic stem or progenitor cells from the individual, and contacting the hematopoietic stem or progenitor cells with a molecule selected from the group consisting of flt-3 ligand, GM-CSF, IL-4, TNF-α, IL-3, c-kit ligand, fusions of GM-CSF and IL-3, and combinations thereof.

3. The method according to claim 2, wherein the CD40 binding protein comprises an oligomer forming peptide and soluble, oligomeric CD40 ligand, wherein the soluble, oligomeric CD40 ligand comprises a polypeptide selected from the group consisting of:
   (a) a polypeptide comprising amino acids 1 through 261, 35 through 261, 34 through 225, 113 through 261, 113 through 225, 120 through 261, or 120 through 225 of SEQ ID NO:2;
   (b) fragments of a polypeptide according to (a) that bind CD40; and
   (c) polypeptides encoded by DNA which hybridizes to a DNA that encodes a peptide of (a) or (b), under stringent conditions (hybridization in 6× SSC at 63° C. overnight; washing in 3× SSC at 55° C.), and which bind to CD40.

4. The method according to claim 3, wherein the soluble, oligomeric CD40 ligand comprises a polypeptide is selected from the group consisting of:
   (a) a polypeptide having an amino acid sequence as set forth in SEQ ID NO:2 wherein a cysteine at amino acid 194 is replaced with another amino acid; and
   (b) a polypeptide that is a fragment of the polypeptide (a) that binds CD40; wherein the amino acid that is substituted for the cysteine at amino acid 194 is selected from the group consisting of tryptophan, serine, aspartic acid, and lysine.

5. The method according to claim 1, wherein flt-3 ligand is administered to the individual prior to obtaining the dendritic cells, to expand the number of progenitor cells in the circulation of the individual.

6. The method according to claim 5, wherein the dendritic cells are obtained by obtaining hematopoietic stem or progenitor cells from the individual, and contacting the hematopoietic stem or progenitor cells with a molecule selected from the group consisting of flt-3 ligand, GM-CSF, IL-4, TNF-α, IL-3, c-kit ligand, fusions of GM-CSF and IL-3, and combinations thereof.

7. The method according to claim 1, wherein the activated dendritic cells are administered simultaneously, sequentially or separately with a molecule selected from the group consisting of Interleukins 1, 2, 3, 4, 5, 6, 7, 10, 12 and 15; granulocyte-macrophage colony stimulating factor, granulocyte colony stimulating factor; a fusion protein comprising Interleukin-3 and granulocyte-macrophage colony stimulating factor; Interferon-γ; TNF; TGF-β; flt-3 ligand; soluble CD40 ligand; soluble CD83; and combinations thereof.

8. The method according to claim 5, wherein the CD40 binding protein comprises an oligomer forming peptide and soluble, oligomeric CD40 ligand, wherein the soluble, oligomeric CD40 ligand comprises a polypeptide selected from the group consisting of:
   (a) a polypeptide comprising amino acids 1 through 261, 35 through 261, 34 through 225, 113 through 261, 113 through 225, 120 through 261, or 120 through 225 of SEQ ID NO:2;
   (b) fragments of a polypeptide according to (a) that bind CD40;
   (c) polypeptides encoded by DNA which hybridizes to a DNA that encodes a polypeptide of (a) or (b), under stringent conditions (hybridization in 6× SSC at 63° C. overnight; washing in 3× SSC at 55° C.), and which bind to CD40;
   (d) a polypeptide according to (a) wherein the cysteine at amino acid 194 is replaced with another amino acid selected from the group consisting of tryptophan, serine, aspartic acid, and lysine; and
   (e) a fragment of the polypeptide of (d) which binds CD40.

9. The method according to claim 6, wherein the CD40 binding protein comprises an oligomer forming peptide and soluble, oligomeric CD40 ligand, wherein the soluble, oligomeric CD401 ligand comprises a polypeptide selected from the group consisting of:
   (a) polypeptide comprising amino acids 1 through 261, 35 through 261, 34 through 225, 113 through 261, 113 through 225, 120 through 261, or 120 through 225 of SEQ ID NO:2;
   (b) fragments of a polypeptide according to (a) that bind CD40;
   (c) polypeptides encoded by DNA which hybridizes to a DNA that encodes a peptide of (a) or (b), under stringent conditions (hybridization in 6× SSC at 63° C. overnight; washing in 3× SSC at 55° C.), and which bind to CD40;
   (d) a polypeptide according to (a) wherein the cysteine at amino acid 194 is replaced with another amino acid selected from the group consisting of tryptophan, serine, aspartic acid, and lysine; and
   (e) a fragment of the polypeptide of (d) which binds CD40.

10. The method according to claim 7, wherein the CD40 binding protein comprises an oligomer forming peptide and soluble, oligomeric CD40 ligand, wherein the soluble, oligomeric CD40 ligand comprises a polypeptide selected from the group consisting of:
    (a) a polypeptide comprising amino acids 1 through 261, 35 through 261, 34 through 225, 113 through 261, 113 through 225, 120 through 261, or 120 through 225 of SEQ ID NO:2;
    (b) fragments of a polypeptide according to (a) that bind CD40;
    (c) polypeptides encoded by DNA which hybridizes to a DNA that encodes a polypeptide of (a) or (b), under stringent conditions (hybridization in 6× SSC at 63° C. overnight; washing in 3× SSC at 55° C.), and which bind to CD40;
    (d) a polypeptide according to (a) wherein the cysteine at amino acid 194 is replaced with another amino acid selected from the group consisting of tryptophan, serine, aspartic acid, and lysine; and
    (e) a fragment of the polypeptide of (d) which binds CD40.

11. A method for stimulating an antigen-specific immune response comprising the steps of:
    (a) obtaining hematopoietic stem or progenitor cells from an individual;
    (b) obtaining dendritic cells by contacting, ex vivo, the cells of step (a) with cytokines suitable for culturing dendritic cells;
    (c) exposing the dendritic cells of step (b) with a gene encoding an antigen, so as to obtain antigen-expressing dendritic cells;
    (d) exposing the antigen-expressing dendritic cells of step (c) to a protein which binds CD40 and inhibits binding of CD40 to CD40L, so as to obtain activated, antigen-expressing dendritic cells; and (e) administering an effective amount of the activated antigen-expressing dendritic cells of step (d) to the individual so as to stimulate the antigen-specific immune response in an individual.

12. The method according to claim 11, wherein the binding protein is selected from the group consisting of:
(a) a soluble, oligomeric CD40 ligand comprising amino acids 1–261 of SEQ ID NO:2 and an oligomer-forming peptide;
(b) a soluble, oligomeric CD40 ligand comprising amino acids 35–261 of SEQ ID NO:2 and an oligomer-forming peptide;
(c) a soluble, oligomeric CD40 ligand comprising amino acids 34–225 of SEQ ID NO:2 and an oligomer-forming peptide;
(d) a soluble, oligomeric CD40 ligand comprising amino acids 113–261 of SEQ ID NO:2 and an oligomer-forming peptide;
(e) a soluble, oligomeric CD40 ligand comprising amino acids 113–225 of SEQ ID NO:2 and an oligomer-forming peptide;
(f) a soluble, oligomeric CD40 ligand comprising amino acids 120–261 of SEQ ID NO:2 and an oligomer-forming peptide;
(g) a soluble, oligomeric CD40 ligand comprising amino acids 120–225 of SEQ ID NO:2 and an oligomer-forming peptide; and
(h) fragments of a polypeptide according to (a)–(g) that bind CD40.

13. The method of claim 12 wherein the oligomer-forming peptide is an immunoglobulin heavy chain encoded by nucleotides 1–740 of SEQ ID NO:3.

14. The method of claim 12 wherein the oligomer-forming peptide is a leucine zipper represented by amino acids 1–33 of SEQ ID NO:4.

15. The method of claim 11 wherein the cysteine at amino acid 194 of SEQ ID NO:2 is substituted with an amino acid selected from the group consisting of tryptophan, serine, aspartic acid and lysine.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 840 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens (vii) IMMEDIATE SOURCE:
    (B) CLONE: CD40-L (ix) FEATURE:
    (A) NAME/KEY: CDS
    (B) LOCATION: 46..831

(xi) SEQUENCE DESCRIPTION: SEQ ID NO:1:

```
TGCCACCTTC TCTGCCAGAA GATACCATTT CAACTTTAAC ACAGC ATG ATC GAA              54
                                                  Met Ile Glu
                                                    1

ACA TAC AAC CAA ACT TCT CCC CGA TCT GCG GCC ACT GGA CTG CCC ATC          102
Thr Tyr Asn Gln Thr Ser Pro Arg Ser Ala Ala Thr Gly Leu Pro Ile
      5                  10                  15

AGC ATG AAA ATT TTT ATG TAT TTA CTT ACT GTT TTT CTT ATC ACC CAG          150
Ser Met Lys Ile Phe Met Tyr Leu Leu Thr Val Phe Leu Ile Thr Gln
 20                  25                  30                  35

ATG ATT GGG TCA GCA CTT TTT GCT GTG TAT CTT CAT AGA AGG TTG GAC          198
Met Ile Gly Ser Ala Leu Phe Ala Val Tyr Leu His Arg Arg Leu Asp
                 40                  45                  50

AAG ATA GAA GAT GAA AGG AAT CTT CAT GAA GAT TTT GTA TTC ATG AAA          246
Lys Ile Glu Asp Glu Arg Asn Leu His Glu Asp Phe Val Phe Met Lys
             55                  60                  65

ACG ATA CAG AGA TGC AAC ACA GGA GAA AGA TCC TTA TCC TTA CTG AAC          294
Thr Ile Gln Arg Cys Asn Thr Gly Glu Arg Ser Leu Ser Leu Leu Asn
         70                  75                  80

TGT GAG GAG ATT AAA AGC CAG TTT GAA GGC TTT GTG AAG GAT ATA ATG          342
Cys Glu Glu Ile Lys Ser Gln Phe Glu Gly Phe Val Lys Asp Ile Met
     85                  90                  95

TTA AAC AAA GAG GAG ACG AAG AAA GAA AAC AGC TTT GAA ATG CAA AAA          390
Leu Asn Lys Glu Glu Thr Lys Lys Glu Asn Ser Phe Glu Met Gln Lys
100                 105                 110                 115

GGT GAT CAG AAT CCT CAA ATT GCG GCA CAT GTC ATA AGT GAG GCC AGC          438
Gly Asp Gln Asn Pro Gln Ile Ala Ala His Val Ile Ser Glu Ala Ser
                 120                 125                 130

AGT AAA ACA ACA TCT GTG TTA CAG TGG GCT GAA AAA GGA TAC TAC ACC          486
Ser Lys Thr Thr Ser Val Leu Gln Trp Ala Glu Lys Gly Tyr Tyr Thr
             135                 140                 145

ATG AGC AAC AAC TTG GTA ACC CTG GAA AAT GGG AAA CAG CTG ACC GTT          534
Met Ser Asn Asn Leu Val Thr Leu Glu Asn Gly Lys Gln Leu Thr Val
         150                 155                 160

AAA AGA CAA GGA CTC TAT TAT ATC TAT GCC CAA GTC ACC TTC TGT TCC          582
Lys Arg Gln Gly Leu Tyr Tyr Ile Tyr Ala Gln Val Thr Phe Cys Ser
     165                 170                 175

AAT CGG GAA GCT TCG AGT CAA GCT CCA TTT ATA GCC AGC CTC TGC CTA          630
Asn Arg Glu Ala Ser Ser Gln Ala Pro Phe Ile Ala Ser Leu Cys Leu
180                 185                 190                 195

AAG TCC CCC GGT AGA TTC GAG AGA ATC TTA CTC AGA GCT GCA AAT ACC          678
Lys Ser Pro Gly Arg Phe Glu Arg Ile Leu Leu Arg Ala Ala Asn Thr
                 200                 205                 210
```

```
CAC AGT TCC GCC AAA CCT TGC GGG CAA CAA TCC ATT CAC TTG GGA GGA         726
His Ser Ser Ala Lys Pro Cys Gly Gln Gln Ser Ile His Leu Gly Gly
            215                 220                 225

GTA TTT GAA TTG CAA CCA GGT GCT TCG GTG TTT GTC AAT GTG ACT GAT         774
Val Phe Glu Leu Gln Pro Gly Ala Ser Val Phe Val Asn Val Thr Asp
            230                 235                 240

CCA AGC CAA GTG AGC CAT GGC ACT GGC TTC ACG TCC TTT GGC TTA CTC         822
Pro Ser Gln Val Ser His Gly Thr Gly Phe Thr Ser Phe Gly Leu Leu
            245                 250                 255

AAA CTC TGAACAGTGT CA                                                   840
Lys Leu
260

(2) INFORMATION FOR SEQ ID NO:2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:2:

Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
                 20                  25                  30

Ile Thr Gln Met Ile Gly Ser Ala Leu Phe Ala Val Tyr Leu His Arg
             35                  40                  45

Arg Leu Asp Lys Ile Glu Asp Glu Arg Asn Leu His Glu Asp Phe Val
         50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

-continued (2) INFORMATION FOR SEQ ID NO:3:

(i) SEQUENCE CHARACTERISTICS:
  (A) LENGTH: 740 base pairs
  (B) TYPE: nucleic acid
  (C) STRANDEDNESS: single
  (D) TOPOLOGY: linear  (ii) MOLECULE TYPE: cDNA  (iii) HYPOTHETICAL: NO  (iv) ANTI-SENSE: NO  (vi) ORIGINAL SOURCE:
  (A) ORGANISM: HUMAN  (vii) IMMEDIATE SOURCE:
  (B) CLONE: IgG1 Fc  (xi) SEQUENCE DESCRIPTION: SEQ ID NO:3:

```
CGGTACCGCT AGCGTCGACA GGCCTAGGAT ATCGATACGT AGAGCCCAGA TCTTGTGACA      60
AAACTCACAC ATGCCCACCG TGCCCAGCAC CTGAACTCCT GGGGGGACCG TCAGTCTTCC     120
TCTTCCCCCC AAAACCCAAG GACACCCTCA TGATCTCCCG GACCCCTGAG GTCACATGCG     180
TGGTGGTGGA CGTGAGCCAC GAAGACCCTG AGGTCAAGTT CAACTGGTAC GTGGACGGCG     240
TGGAGGTGCA TAATGCCAAG ACAAAGCCGC GGGAGGAGCA GTACAACAGC ACGTACCGGG     300
TGGTCAGCGT CCTCACCGTC CTGCACCAGG ACTGGCTGAA TGGCAAGGAC TACAAGTGCA     360
AGGTCTCCAA CAAAGCCCTC CCAGCCCCCA TGCAGAAAAC CATCTCCAAA GCCAAAGGGC     420
AGCCCCGAGA ACCACAGGTG TACACCCTGC CCCCATCCCG GGATGAGCTG ACCAAGAACC     480
AGGTCAGCCT GACCTGCCTG GTCAAAGGCT TCTATCCCAG CGACATCGCC GTGGAGTGGG     540
AGAGCAATGG GCAGCCGGAG AACAACTACA AGACCACGCC TCCCGTGCTG GACTCCGACG     600
GCTCCTTCTT CCTCTACAGC AAGCTCACCG TGGACAAGAG CAGGTGGCAG CAGGGGAACG     660
TCTTCTCATG CTCCGTGATG CATGAGGCTC TGCACAACCA CTACACGCAG AAGAGCCTCT     720
CCCTGTCTCC GGGTAAATGA                                                740
```

(2) INFORMATION FOR SEQ ID NO:4:

(i) SEQUENCE CHARACTERISTICS:
  (A) LENGTH: 33 amino acids
  (B) TYPE: amino acid
  (D) TOPOLOGY: linear  (ii) MOLECULE TYPE: peptide  (xi) SEQUENCE DESCRIPTION: SEQ ID NO:4:

```
Arg Met Lys Gln Ile Glu Asp Lys Ile Glu Glu Ile Leu Ser Lys Ile
1               5                  10                  15
Tyr His Ile Glu Asn Glu Ile Ala Arg Ile Lys Lys Leu Ile Gly Glu
            20                  25                  30
Arg
```